(12) United States Patent
Ludwig (10) Patent No.: US 10,498,939 B2
(45) Date of Patent: Dec. 3, 2019

(54) SMALL-PROFILE LENSLESS OPTICAL MICROSCOPY IMAGING AND TOMOGRAPHY INSTRUMENTS AND ELEMENTS FOR LOW COST AND INTEGRATED MICROSCOPY

(71) Applicant: Lester F. Ludwig, San Antonio, TX (US)

(72) Inventor: Lester F. Ludwig, San Antonio, TX (US)

(73) Assignee: NRI R&D Patent Licensing, LLC, San Antonio, TX (US)

( * ) Notice: Subject to any disclaimer, the term of this patent is extended or adjusted under 35 U.S.C. 154(b) by 0 days.

(21) Appl. No.: 14/105,108

(22) Filed: Dec. 12, 2013

(65) Prior Publication Data
US 2014/0092229 A1    Apr. 3, 2014

Related U.S. Application Data

(63) Continuation-in-part of application No. 12/817,107, filed on Jun. 16, 2010.
(Continued)

(51) Int. Cl.
*H04N 5/225* (2006.01)
*G01N 15/14* (2006.01)
(Continued)

(52) U.S. Cl.
CPC ....... *H04N 5/2256* (2013.01); *G01N 15/1475* (2013.01); *G02B 21/0008* (2013.01); *G02B 21/365* (2013.01)

(58) Field of Classification Search
CPC ..... A61B 3/102; A61B 5/0066; A61B 3/0025; A61B 3/113; A61B 6/485; A61B 3/10;
(Continued)

(56) References Cited

U.S. PATENT DOCUMENTS

5,513,237 A * 4/1996 Nobuta ................ A61B 5/0456
378/19
5,566,218 A * 10/1996 Nobuta ................ A61B 5/0456
378/117
(Continued)

*Primary Examiner* — Dave Czekaj
*Assistant Examiner* — Kehinde Abimbola (57) ABSTRACT

Arrangements for small-sized, inexpensive, and innovative lensless and other micro-optic microscopy imaging and tomography are presented. An imaging region comprising flat or curved surfaces is provided with an illumination source proximate to the imaging region or arranged for collimated illumination. Light travels through the imaging region and produces a resulting light field affected by objects, materials, fluids, organisms, etc. in the light path and is presented to an image sensing surface proximate to the imaging region, responsively creating electrical image signals. The illumination surface can be light emitting elements such as LEDs, OLEDs, or OLET whose illumination can be sequenced in an image formation or tomography process. Light-emission and light detection elements can be printed, permitting extremely low-cost manufacturing and readily accommodating imaging regions having curved shapes. Applications include laboratory instruments, microarrays, microplates, flow microscopes, cytometry systems, environmental and contamination monitoring systems, industrial monitoring instruments, food safety systems, and implants.

20 Claims, 8 Drawing Sheets

Related U.S. Application Data (60) Provisional application No. 61/268,900, filed on Jun. 16, 2009.

(51) Int. Cl.
*G02B 21/00* (2006.01)
*G02B 21/36* (2006.01)

(58) Field of Classification Search
CPC .. A61B 3/112; G06K 9/00127; G06K 9/4647; G06K 2009/2045; G06K 9/00134; G01N 2035/00326; G01N 2035/00495; G01N 35/0092; G01N 2015/1006; G01N 35/10; G01N 35/00871; G01N 35/1065; G01N 21/25; G01N 33/92; G01N 35/1072; G01N 15/1475; G01N 2035/00138; G01N 2035/00356; H01L 2924/00; H01L 2924/0002; H01L 2224/48091; H01L 25/0753; H01L 2924/10253; H01L 21/6838; H01L 33/44; H01L 33/58; H01L 21/0237; H01L 21/0243; H01L 21/02458; H01L 21/0254; H04B 3/54; H04B 3/52; H04B 3/56; H04B 10/40; H04B 10/5161; H04B 10/541; H04B 2203/5425
See application file for complete search history.

(56) References Cited

U.S. PATENT DOCUMENTS

| | | | | |
|---|---|---|---|---|
| 5,608,772 | A * | 3/1997 | Nobuta | A61B 5/0456 378/116 |
| 5,627,868 | A * | 5/1997 | Nobuta | A61B 5/0456 378/19 |
| 5,726,443 | A * | 3/1998 | Immega | G01S 17/026 250/208.1 |
| 6,034,703 | A * | 3/2000 | Broddin | B41J 2/385 347/131 |
| 6,262,818 | B1 * | 7/2001 | Cuche | G03H 1/0443 359/10 |
| 7,176,685 | B2 * | 2/2007 | Blasche | 324/309 |
| 7,554,572 | B2 * | 6/2009 | Takahashi | 348/65 |
| 7,627,193 | B2 * | 12/2009 | Alon et al. | 382/275 |
| 7,857,224 | B2 * | 12/2010 | Lei | G06K 7/10851 235/462.42 |
| 7,961,323 | B2 * | 6/2011 | Tibbetts | 356/417 |
| 8,184,279 | B2 * | 5/2012 | Feldkhun | G01N 21/6458 250/351 |
| 8,194,124 | B2 * | 6/2012 | Asundi et al. | 348/79 |
| 8,284,492 | B2 * | 10/2012 | Crane | B41M 3/003 359/620 |
| 8,314,933 | B2 * | 11/2012 | Cui | G01N 21/6458 356/436 |
| 8,325,349 | B2 * | 12/2012 | Cui | G02B 21/33 356/515 |
| 8,416,400 | B2 * | 4/2013 | Cui | G01J 9/0215 356/121 |
| 8,660,312 | B2 * | 2/2014 | Cui | G01B 11/2441 382/106 |
| 8,964,020 | B2 * | 2/2015 | Hersee | G02B 21/002 348/79 |
| 9,426,429 | B2 * | 8/2016 | Zheng | G02B 21/06 |
| 2002/0075481 | A1 * | 6/2002 | Roustaei | 356/388 |
| 2003/0086598 | A1 * | 5/2003 | Blasche | 382/131 |
| 2005/0110725 | A1 * | 5/2005 | Kwak et al. | 345/76 |
| 2005/0219229 | A1 * | 10/2005 | Yamaguchi | G06F 3/0412 345/173 |
| 2005/0264672 | A1 * | 12/2005 | Takahashi | 348/335 |
| 2006/0256226 | A1 * | 11/2006 | Alon et al. | 348/335 |
| 2007/0273143 | A1 * | 11/2007 | Crane | B41M 3/003 283/72 |
| 2008/0100642 | A1 * | 5/2008 | Betancourt et al. | 345/663 |
| 2008/0105746 | A1 * | 5/2008 | Lei | G06K 7/10722 235/462.11 |
| 2009/0091811 | A1 * | 4/2009 | Asundi | G02B 21/36 359/15 |
| 2009/0316141 | A1 * | 12/2009 | Feldkhun | G01N 21/6458 356/217 |
| 2010/0033561 | A1 * | 2/2010 | Hersee | G02B 21/002 348/80 |
| 2010/0195873 | A1 * | 8/2010 | Cui | G01B 11/2441 382/106 |
| 2011/0170105 | A1 * | 7/2011 | Cui | G02B 21/33 356/450 |
| 2011/0181884 | A1 * | 7/2011 | Cui | G01N 21/53 356/436 |
| 2012/0098950 | A1 * | 4/2012 | Zheng | G02B 21/06 348/79 |
| 2012/0257197 | A1 * | 10/2012 | Feldkhun | G01N 21/4795 356/301 |
| 2017/0316713 | A1 * | 11/2017 | Hyman | B44C 3/046 |

\* cited by examiner

Figure 1

|  | pixels / sq.mm | mm/px | µm/px | # pixels | Amoeba - 700µm | Amoeba - 1000µm | sensor area size (sq.mm) |
|---|---|---|---|---|---|---|---|
| Andanta Ultra-High Res CCD | 4933 | 0.00020272 | 0.2027164 | 111000000 | 3453.1 | 4933 | 22500 |
| Megaplus ER 11000 (lower) | 12732 | 7.8542E-05 | 0.07854226 | 11000000 | 8912.4 | 12732 | 864 |
| Megaplus ER 11000 (upper) | 111111 | 9E-06 | 0.00900001 | 96000000 | 77777.7 | 111111 | 864 |
| Kodak KAI-11002 | 12458 | 8.027E-05 | 0.08026971 | 11100000 | 8720.6 | 12458 | 891 |
| DCU 223 M/C Sony | 10971 | 9.1149E-05 | 0.09114939 | 786432 | 7679.7 | 10971 | 71.68 |
| DCU 224 M/C Sony | 8126 | 0.00012306 | 0.12306178 | 1310720 | 5688.2 | 8126 | 161.28 |
| Kodak KAI-08050 | 33653 | 2.9715E-05 | 0.02971503 | 8147712 | 23557.1 | 33653 | 242.11 |

Figure 2a

|  | pixels / sq.mm | mm/px | µm/px | # pixels | Protozoa (type A) - 10µm | Protozoa (type B) - 50µm | Protozoa (type C) - 1000µm | sensor area size (sq.mm) |
|---|---|---|---|---|---|---|---|---|
| Andanta Ultra-High Res CCD | 4933 | 0.00020272 | 0.2027164 | 111000000 | 49.33 | 246.65 | 4933 | 22500 |
| Megaplus ER 11000 (lower) | 12732 | 7.8542E-05 | 0.07854226 | 11000000 | 127.32 | 636.6 | 12732 | 864 |
| Megaplus ER 11000 (upper) | 111111 | 9E-06 | 0.00900001 | 96000000 | 1111.11 | 5555.55 | 111111 | 864 |
| Kodak KAI-11002 | 12458 | 8.027E-05 | 0.08026971 | 11100000 | 124.58 | 622.9 | 12458 | 891 |
| DCU 223 M/C Sony | 10971 | 9.1149E-05 | 0.09114939 | 786432 | 109.71 | 548.55 | 10971 | 71.68 |
| DCU 224 M/C Sony | 8126 | 0.00012306 | 0.12306178 | 1310720 | 81.26 | 406.3 | 8126 | 161.28 |
| Kodak KAI-08050 | 33653 | 2.9715E-05 | 0.02971503 | 8147712 | 336.53 | 1682.65 | 33653 | 242.11 |

Figure 2b

|  | pixels / sq.mm | mm/px | μm/px | # pixels | Rotifiers (type A) - 100μm | Rotifiers (type A) - 500μm | Rotifiers (type B) - 50μm | Rotifiers (type B) - 2000μm | sensor area size (sq.mm) |
|---|---|---|---|---|---|---|---|---|---|
| Andanta Ultra-High Res CCD | 4933 | 0.00020272 | 0.2027164 | 111000000 | 493.3 | 2466.5 | 246.65 | 9866 | 22500 |
| Megaplus ER 11000 (lower) | 12732 | 7.8542E-05 | 0.07854226 | 11000000 | 1273.2 | 6366 | 636.6 | 25464 | 864 |
| Megaplus ER 11000 (upper) | 111111 | 9E-06 | 0.00900001 | 96000000 | 11111.1 | 55555.5 | 5555.55 | 222222 | 864 |
| Kodak KAI-11002 | 12458 | 8.027E-05 | 0.08026971 | 11100000 | 1245.8 | 6229 | 622.9 | 24916 | 891 |
| DCU 223 M/C Sony | 10971 | 9.1149E-05 | 0.09114939 | 786432 | 1097.1 | 5485.5 | 548.55 | 21942 | 71.68 |
| DCU 224 M/C Sony | 8126 | 0.00012306 | 0.12306178 | 1310720 | 812.6 | 4063 | 406.3 | 16252 | 161.28 |
| Kodak KAI-08050 | 33653 | 2.9715E-05 | 0.02971503 | 8147712 | 3365.3 | 16826.5 | 1682.65 | 67306 | 242.11 |

Figure 2c

|  | pixels / sq.mm | mm/px | μm/px | # pixels | Amoeba 700μm | Amoeba 1000μm |
|---|---|---|---|---|---|---|
| Canon D30, 3MP | 95.4 | 0.0104822 | 10.48218 | 3000000 | 66.78 | 95.4 |
| Nikon Coolpix 995, 3MP | 290 | 0.0034483 | 3.4482759 | 3000000 | 203 | 290 |
| Minolta Xi, 3MP | 384 | 0.0026042 | 2.6041667 | 3000000 | 268.8 | 384 |
| OmniVision OV5620, 5MP |  |  | 2.2 | 5000000 | 318.1818 | 454.5455 |
| OmniVision OV5630/5633, 5MP |  |  | 1.75 | 5000000 | 400 | 571.4286 |
| OmniVision OV8810/8812, 8MP |  |  | 1.4 | 8000000 | 500 | 714.2857 |

SMALL-PROFILE LENSLESS OPTICAL MICROSCOPY IMAGING AND TOMOGRAPHY INSTRUMENTS AND ELEMENTS FOR LOW COST AND INTEGRATED MICROSCOPY

CROSS-REFERENCE TO RELATED APPLICATIONS

This application is a Continuation in Part of U.S. patent application Ser. No. 12/817,107, filed Jun. 16, 2010, and claims benefit of priority of U.S. Provisional Application No. 61/268,900, filed on Jun. 16, 2009, both of which are incorporated herein by reference.

BACKGROUND OF THE INVENTION

Field of the Invention

The present invention generally relates to electronic cameras, electronic imaging, fluid flow microscopes, image processing, and in particular to how these can be combined in various ways to create small low-power inexpensive microscope and optical tomography elements for use in a variety of applications.

The present invention provides for small-sized, inexpensive, and innovative electronic imaging arrangements used for lensless and other micro-optic microscopy imaging and tomography.

Background

U.S. patent application Ser. No. 12/817,107 provided description of lensless microscope imaging that can be used, for example, to visually monitor micro-organism and other microscopic affairs in various applications. As stated therein, the resulting arrangement can be physically small, sturdy, low-energy consuming, easy to use, inexpensive, and remotely controllable by electrical or data signals.

The present application expands this approach. The invention provides for small-sized, inexpensive, and innovative electronic imaging arrangements used for lensless and other micro-optic microscopy imaging and tomography.

Both the systems and methods taught in U.S. patent application Ser. No. 12/817,107 and the systems and methods of the present application can be implemented or adapted for use as a stand-alone laboratory instrument or for use as a component in other equipment, including micro-arrays, microplates, flow microscopes, cytometry systems, environmental and contamination monitoring systems, industrial monitoring instruments, food safety systems, etc.

The arrangement can also be configured to be implanted or otherwise introduced into the body of an animal, plant, or human.

SUMMARY OF THE INVENTION

In an example embodiment, the invention comprises a transparent imaging region. The imaging region can comprise or accommodate, or be comprised within, a microscope slide, fluid transport arrangement, micro-array, microplate, small hand-held device, cytometry system, industrial machinery, etc. In one embodiment the imaging region comprises two parallel flat sides, although curved surfaces can also be used. An illumination source can be provided and in some embodiments can be arranged to be proximate or in contact with one side of the imaging region. An image sensing surface can be arranged to be proximate or in contact with the other side of the imaging region for receiving light fields and responsively creating electrical image signals.

Light from the illumination source travels into the imaging region and produces a resulting light field affected by objects, materials, fluids, organisms, etc. in the light path through the imaging region. At least portions of the resulting light field is presented to one or more image sensing surfaces that create electrical image signals responsive to the resulting light field.

The imaging sensor can be implemented (with or without lenses) in a 2-dimensional manner similar to the 1-dimensional imaging arrangements of a document scanner. The source of illumination can be a light-emitting array, and the spatial light distribution can be fixed, time-varying, or modulated. For example, the illumination surface can be individual light-emitting pixels wherein the individual light-emitting pixels can be sequenced. Such sequencing permits spatial light field measurements that can be used in optical tomography. Accordingly, the invention provides data that can be used for optical tomography or used to produce tomography output.

The light-emitting array can provide sequenced spatially modulated illumination, the sequence operated as part of an imaging system producing fully-formed image output. In such embodiments, the array can produce a partially-formed image output that can be subsequent processed by another processor to produce fully-formed image output.

In some imaging implementations and applications, the material being imaged in the imaging region is thin in one dimension, for example as is commonly the case on conventional optical microscope slides. In such implementations and applications, the imaging sensing surface is configured to receive collimated light, or is proximate enough to the material being imaged in the imaging region that the light passing through the material being imaged in the imaging region is nearly collimated.

In such arrangements where the light passing through the material in the imaging region is nearly collimated or not collimated, algorithm-based lensless image formation algorithms, for example as taught in Pending U.S. patent application Ser. No. 12/419,229 (priority dates 1998-1999), Pending U.S. patent application Ser. No. 13/452,461 (priority date Apr. 20, 2011), and U.S. Pat. No. 8,305,480 (priority date May 22, 2008) can be used. As taught in Pending U.S. patent application Ser. No. 12/419,229, the algorithm-based lensless image formation arrangements and algorithms can include refraction effects, frequency domain techniques, deconvolution techniques, approximations, and employ a variety of micro-optic arrangements.

In an example embodiment, a lensless microscopic imaging system for providing imaging, tomography, or both imaging and tomography of microscopic-scale objects is implemented, the microscopic imaging system comprising:

A imaging region comprising at least two transparent sides or areas;

A illumination surface in contact with one of the sides or areas of the imaging region; and A image sensing surface proximate with another of the sides or areas of the imaging region, the image sensing surface receiving light fields from the image sensing surface and responsively creating electrical image signals;

wherein light from the illumination surface travels into the imaging region, producing a resulting light field affected by the contents of the imaging region, wherein the resulting light field is presented to the image sensing surface, and wherein the image sensing surface creates electrical image signals responsive to the resulting light field, and wherein the image sensing surface comprises no lenses and the light path between the imaging region and the image sensing surface does not pass through a lens element.

The present invention can be implemented or adapted for use as a stand-alone laboratory instrument or for use as a component in other equipment, including micro-arrays, microplates, flow microscopes, cytometry systems, environmental and contamination monitoring systems, industrial monitoring instruments, food safety systems, etc. The arrangement can also be configured to be implanted or otherwise introduced into the body of an animal, plant, or human.

BRIEF DESCRIPTION OF THE DRAWINGS

The above and other aspects, features, and advantages of the present invention will become more apparent upon consideration of the following description of preferred embodiments, taken in conjunction with the accompanying drawing figures.

FIG. 4b depicts the exemplary single-cell organism in comparison an exemplary image sensor pixel array spacing of twice the resolution of that in FIG. 4a.

FIG. 4c depicts the exemplary single-cell organism in comparison an exemplary image sensor pixel array spacing of four times the resolution of that in FIG. 4a.

DETAILED DESCRIPTION

In the following detailed description, reference is made to the accompanying drawing figures which form a part hereof, and which show by way of illustration specific embodiments of the invention. It is to be understood by those of ordinary skill in this technological field that other embodiments can be utilized, and structural, electrical, as well as procedural changes can be made without departing from the scope of the present invention. Wherever possible, the same element reference numbers will be used throughout the drawings to refer to the same or similar parts.

The present invention is an electronic imaging flow-microscope for use in applications such as environmental remote telemetry sensing and bioreactor process monitoring. The invention can also be used in a wide range of other applications, such as monitoring in manufacturing processes or monitoring body fluids in medical applications.

Figure 1:
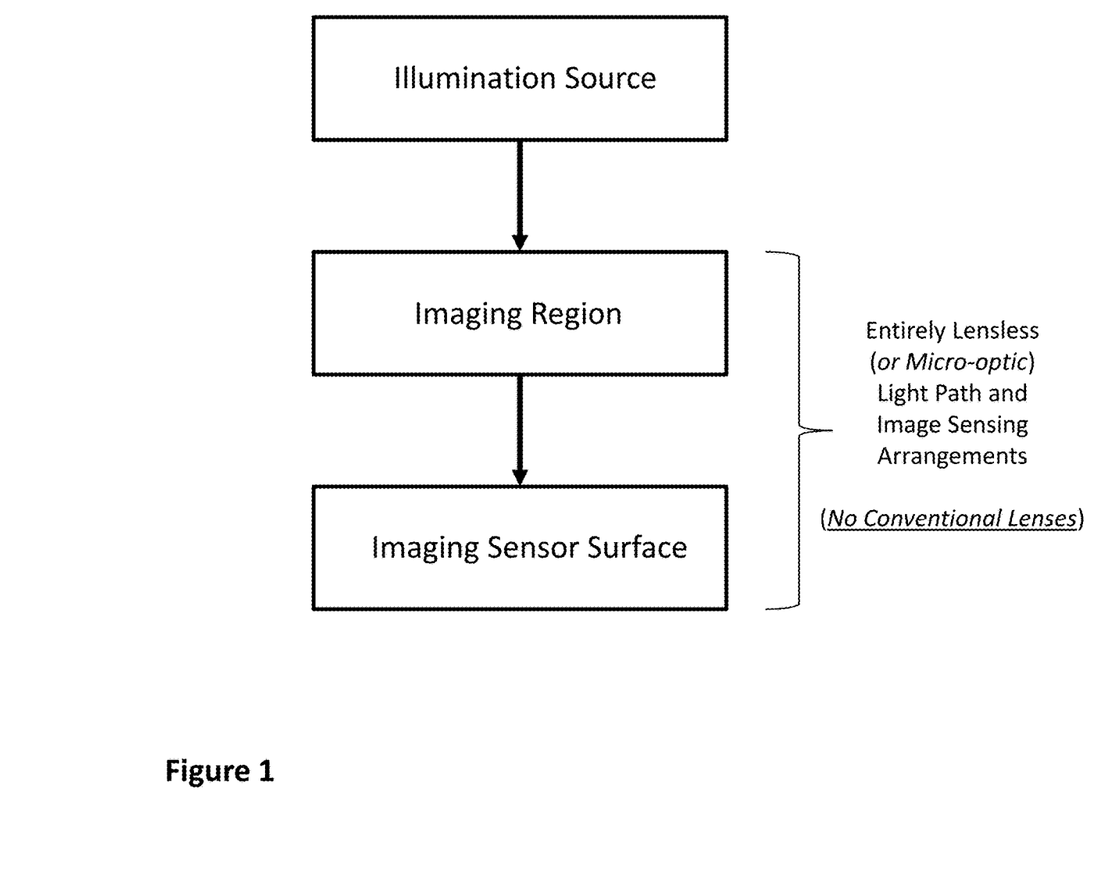
FIG. 1 depicts an exemplary embodiment of the invention with exemplary features.

FIG. 1a depicts a high-level overview representation of features of the invention.

In an embodiment the invention comprises an imaging region with at least two transparent sides or areas. The imaging region can comprise or accommodate, or be comprised within, a microscope slide, fluid transport arrangement, micro-array, microplate, small hand-held device, cytometry system, industrial machinery, etc. In one embodiment the imaging region comprises two parallel flat sides, although curved surfaces can also be used. An illumination source can be provided and can be arranged to be proximate or in contact with one side of the imaging region. An image sensing surface can be arranged to be proximate or in contact with the other side of the imaging region for receiving light fields and responsively creating electrical image signals. Light from the illumination source travels into the imaging region and produces a resulting light field affected by objects, materials, fluids, organisms, etc. in the light path through the imaging region. At least portions of the resulting light field is presented to one or more image sensing surfaces that create electrical image signals responsive to the resulting light field.

The imaging sensor can be implemented (with or without lenses) in a 2-dimensional manner similar to the 1-dimensional imaging arrangements of a document scanner. The source of illumination can be a light-emitting array, and the spatial light distribution can be fixed, time-varying, or modulated. For example, the illumination surface can be individual light-emitting pixels wherein the individual light-emitting pixels can be sequenced. Such sequencing permits spatial light field measurements that can be used in optical tomography. Accordingly, the invention provides data that can be used for optical tomography or used to produce tomography output.

The light-emitting array can provide sequenced spatially modulated illumination, the sequence operated as part of an imaging system producing fully-formed image output. In such embodiments, the array can produce a partially-formed image output that can be subsequent processed by another processor to produce fully-formed image output.

In some imaging implementations and applications, the material being imaged in the imaging region is thin in one dimension, for example as is commonly the case on conventional optical microscope slides. In such implementations and applications, the imaging sensing surface is configured to receive collimated light, or is proximate enough to the material being imaged in the imaging region that the light passing through the material being imaged in the imaging region is nearly collimated.

In such arrangements where the light passing through the material in the imaging region is nearly collimated or not collimated, algorithm-based lensless image formation algorithms, for example as taught in Pending U.S. patent application Ser. No. 12/419,229 (priority dates 1998-1999), Pending U.S. patent application Ser. No. 13/452,461 (priority date Apr. 20, 2011), and U.S. Pat. No. 8,305,480 (priority date May 22, 2008) can be used. As taught in Pending U.S. patent application Ser. No. 12/419,229, the algorithm-based lensless image formation arrangements and algorithms can include refraction effects, frequency domain techniques, deconvolution techniques, approximations, and employ a variety of micro-optic arrangements.

The present invention can be implemented or adapted for use as a stand-alone laboratory instrument or for use as a component in other equipment, including micro-arrays, microplates, flow microscopes, cytometry systems, environmental and contamination monitoring systems, industrial monitoring instruments, food safety systems, etc. The arrangement can also be configured to be implanted or otherwise introduced into the body of an animal, plant, or human.

Further, the imaging systems can be configured provide a platform for various types of optical microscopic tomography. Tomography arrangements are taught in U.S. patent application Ser. No. 12/817,107 and in pending U.S. patent application Ser. Nos. 13/963,917 and 13/963,931, both filed Aug. 9, 2013.

The invention can be used in a wide range of other applications, such as monitoring in manufacturing processes or monitoring body fluids in medical applications.

Overall, the invention opens a very wide set of new possibilities and applications in the areas of microbiology, micro-fabrication, etc.

The invention provides for small-sized, inexpensive, and innovative electronic imaging arrangements used for lensless and other micro-optic microscopy imaging and tomography. In an example embodiment, imaging sensing can be implemented without lenses in a 2-dimensional manner similar to the 1-dimensional imaging arrangements of a document scanner. In these approaches, effectively each image sensor pixel captures immediately emerging light from the fluid or its contents as will be explained. The various arrangements that can be used to leverage and exploit this optical arrangement can also be used to provide a platform for various types of optical microscopic tomography.

To begin, attention is first directed to a representative sample of the state of the art in high-resolution image sensor elements and comparing the direct-contact pixel count and spatial distribution to imaging of some representative one-celled organisms that would be of interest in monitoring environmental water conditions.

Figure 2A:
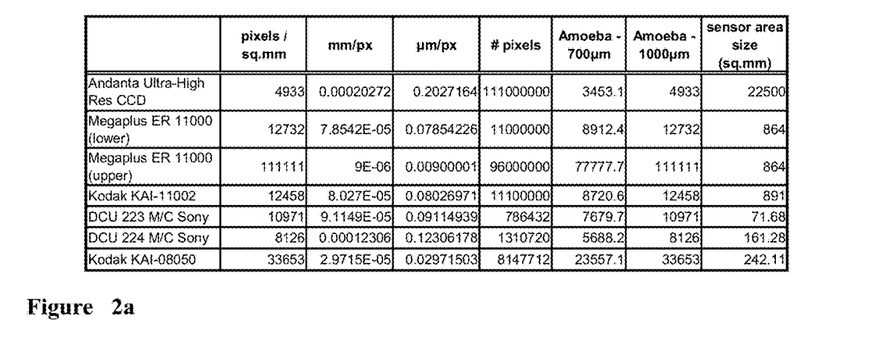
FIG. 2a is a table comparing attributes example contemporary high-resolution optical image-sensing element products to the width of example Amoeba sizes.

FIG. 2a is a table comparing attributes example contemporary high-resolution optical image-sensing element products to the width of example Amoeba sizes. Each row in the table represents an example commercial image sensor product whose resolution (indicated in column 5) ranges from 786,432 pixels to 11.1 million pixels. The spatial distribution of the pixels for each product is compared to the size of larger type of Amoeba, ranging from 700 micro-meters to 1000 micro-meters. The 6th and 7th column of the table represent how many pixels would be sufficient to cover the physical area of the size of one Amoeba.

Figure 2B:
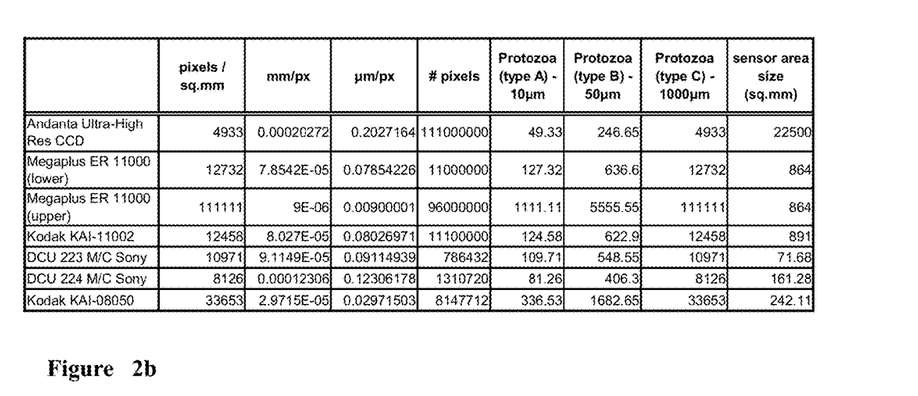
FIG. 2b is a table comparing attributes example contemporary high-resolution optical image-sensing element products to the width of example Protozoa sizes.

FIG. 2b is a table comparing attributes example contemporary high-resolution optical image-sensing element products to the width of example Protozoa sizes. This table is similar but directed to various sizes of Protozoa, which typically ranges from 10 to 1000 micro-meters. The 6th, 7th, and 8th column of the table represent how many pixels would be sufficient to cover the physical area of the size of one Protozoa.

Figure 2C:
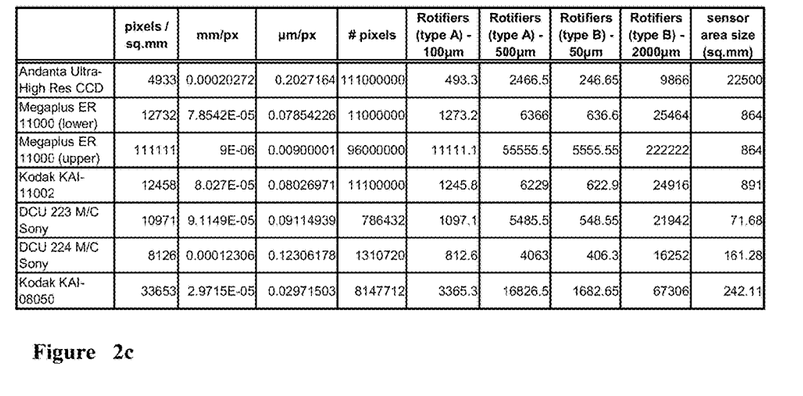
FIG. 2c is a table comparing attributes example contemporary high-resolution optical image-sensing element products to the width of example Rotifer sizes.

FIG. 2c is a table comparing attributes example contemporary high-resolution optical image-sensing element products to the width of example Rotifer sizes. The size of one type of Rotifier typically ranges 100 to 500 micro-meters, and that of another type ranges from 50 to 2000 micrometers. The 6th, 7th, and 8th columns of the table represent how many pixels would be sufficient to cover the physical area of the size of one Rotifier.

In summary, the current state of the art in image sensor products can produce "direct contact" images that would display at the following sizes on contemporary computer monitors:

Protozoa 10 μm in size
   Andanta Ultra-High Res CCD with 11.1 mega-pixel
      13.05 mm (0.51") on a Windows system
      17.40 mm (0.69") on an Apple/Macintosh system
   Megaplus ER 11000 with 96 mega-pixel
      293.99 mm (11.57") on a Windows system
      391.98 mm (15.43") on an Apple/Macintosh system
Amoeba 700 μm in size
   Andanta Ultra-High Res CCD with 11.1 mega-pixel
      913.66 mm (35.97") on a Windows system
      1218.19 mm (47.96") on an Apple/Macintosh system
   Megaplus ER 11000 with 96 mega-pixel
      20579.34 mm (810.21") on a Windows system
      27438.46 mm (1080.25") on an Apple/Macintosh system
Rotifiers 2000 μm in size
   Andanta Ultra-High Res CCD with 11.1 mega-pixel
      2610.46 mm (103") on a Windows system
      3480.53 mm (137") on an Apple/Macintosh system
   Megaplus ER 11000 with 96 mega-pixel
      58798.12 mm (2315") on a Windows system
      78395.61 mm (3086") on an Apple/Macintosh system The above calculations are based on Microsoft Windows operating system default display "DPI" of 96 PPI (one pixel occupies 0.2646 millimeters on the display screen) and Apple/Macintosh default of 72 PPI (one pixel occupies 0.3528 millimeters on the display screen).

Thus contemporary image sensors provide adequate resolution to provide usable 2-dimensional contact imaging at the scale of microorganisms of interest.

Figure 3:
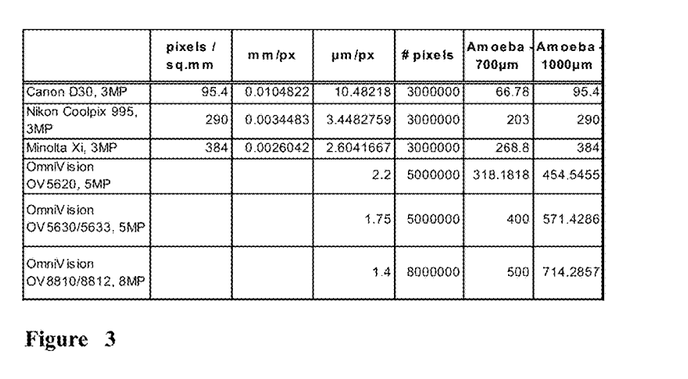
FIG. 3 is a table comparing attributes example contemporary miniature inexpensive cell-phone camera image-sensing element products to the width of example Amoeba sizes.

Additionally it is noted that the resolution and pixel-count of electronic image sensors (CCD, CMOS, photodiode, etc.) continues to improve annually, increasing the number of pixels that can be used to directly observe such microscopic organisms. On the contrary, some of the image sensors of older digital cameras of lower resolution are found to be insufficient. FIG. 3 is a table comparing attributes example contemporary miniature inexpensive cell-phone camera image-sensing element products to the width of example Amoeba sizes. The 6th and 7th column of the table represent how many pixels would be sufficient to cover the physical area of the size of one Amoeba, and such numbers are significantly lower than the models of camera discussed in earlier tables.

Figure 4A:
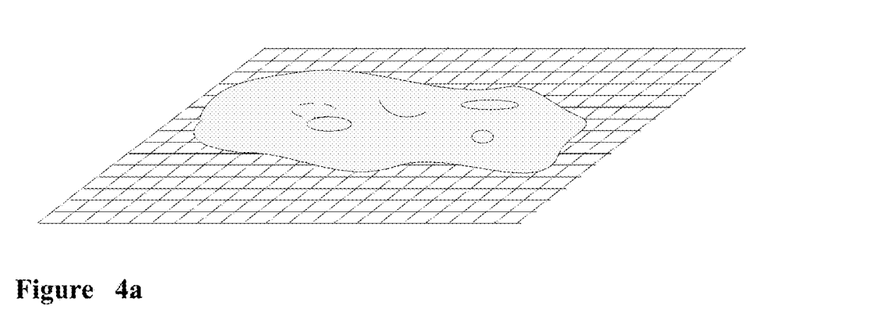
FIG. 4a depicts an exemplary single-cell organism in comparison with an exemplary image sensor pixel array spacing.
Figure 4B:
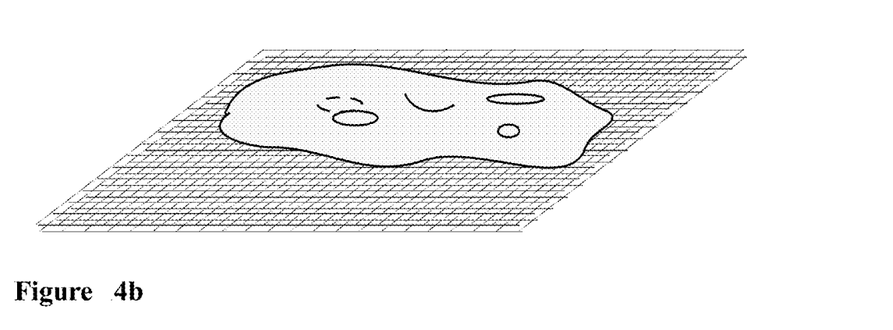
Figure 4C:
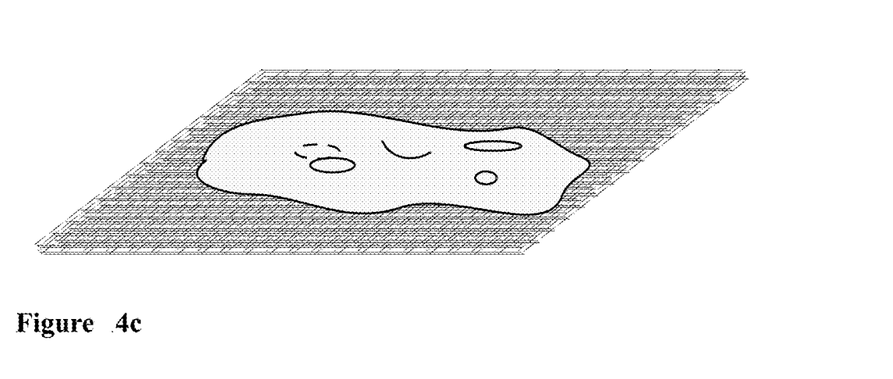

Further as to the use of contemporary image sensors for 2-dimensional contact imaging at the scale of microorganisms of interest, for the sake of illustration FIG. 4a depicts an exemplary single-cell organism in comparison an exemplary image sensor pixel array spacing, while FIG. 4b depicts the exemplary single-cell organism in comparison an exemplary image sensor pixel array spacing of twice the resolution and FIG. 4c depicts the exemplary single-cell organism in comparison an exemplary image sensor pixel array spacing of four times the resolution.

Figure 5:
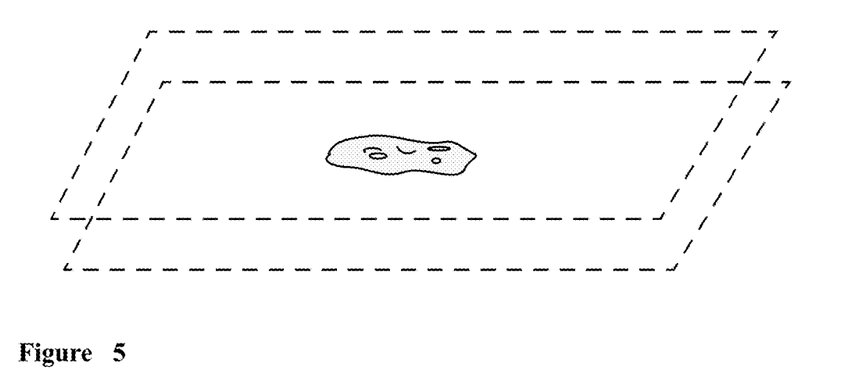
FIG. 5 depicts an exemplary single-cell organism in a fluid region between an illumination surface (top) and an adjacent sensing surface (bottom).

Attention is now directed to FIG. 5 which depicts an exemplary single-cell organism in a fluid region between a illumination surface (top) and an adjacent image sensing surface (bottom). The illumination surface can be a uniformly lit optically diffused light source, a structured collimated light source, etc.

Figure 6:
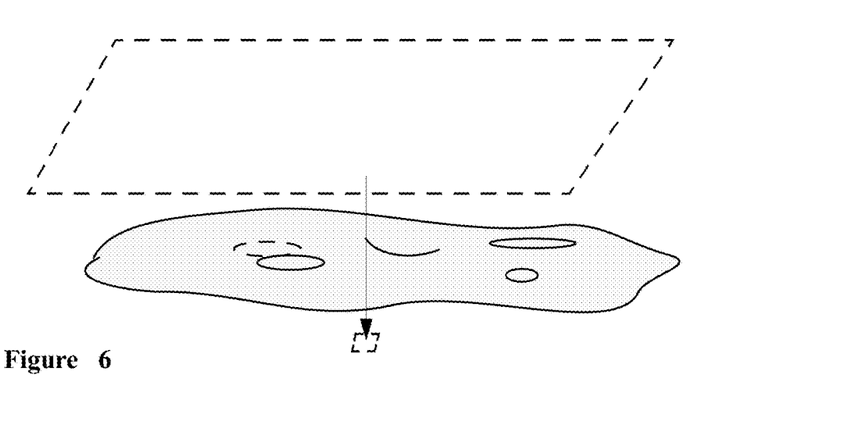
FIG. 6 depicts an exemplary straight light path through an exemplary translucent single-cell organism in a fluid region from an exemplary first area of the illumination surface to an exemplary pixel in the image sensor.
Figure 7:
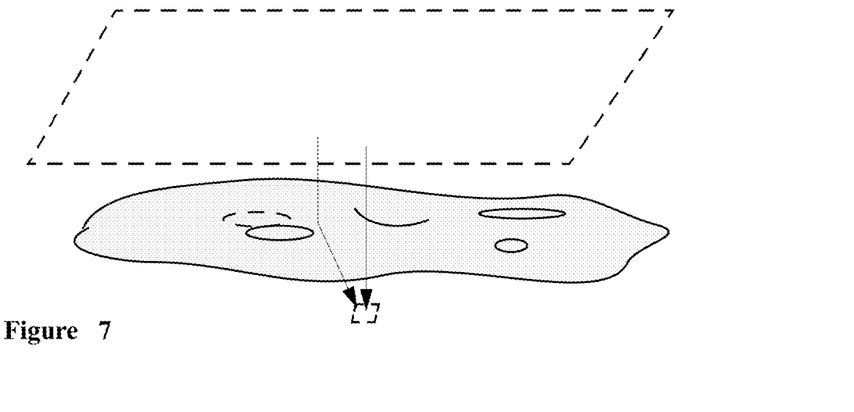
FIG. 7 depicts an augmentation of FIG. 6 also including an exemplary bent light path through an exemplary translucent single-cell organism in a fluid region from an exemplary second area of the illumination surface to an exemplary pixel in the image sensor.

FIG. 6 depicts an exemplary straight light path through an exemplary translucent single-cell organism in a fluid region from a first area of the illumination surface to a pixel in the image sensor. Such a light path would be produced by either a collimated or a optically diffused light source. As a next step, FIG. 7 depicts an augmentation of FIG. 6 which also includes a bent light path through the translucent single-cell organism in a fluid region from a second area of the illumination surface to a pixel in the image sensor. The image sensor pixel received the sum of both light paths, thus contributing to a lack of sharpness of the captured image and potentially other effects. It is noted that there is a huge distribution of such bent light paths, even with a collimated light source.

Figure 8:
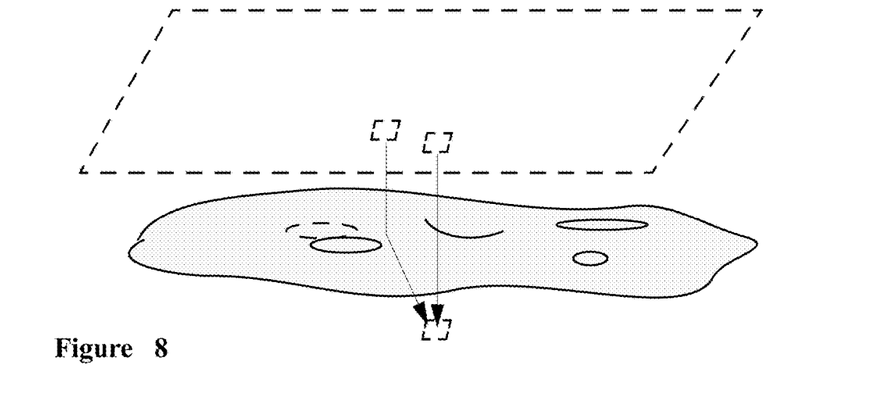
FIG. 8 depicts an adaptation of the situation depicted in FIG. 7 wherein the illumination surface comprises individual light-emitting pixels, one which serves as the exemplary first area of the illumination surface and the other of which serves as the exemplary second area of the illumination surface.
Figure 9:
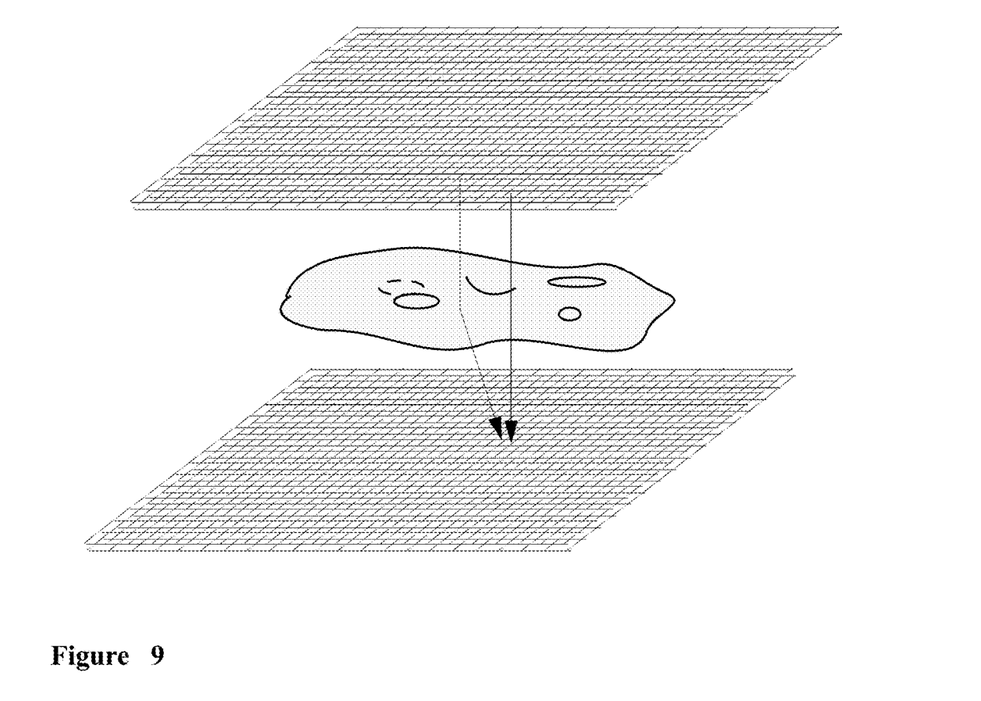
FIG. 9 depicts a larger scale view of the situation depicted in FIG. 8 wherein the illumination surface is an array of light-emitting elements and areas of both the illumination array and the image sensor array are depicted.

To address this, FIG. 8 depicts an adaptation of the situation depicted in FIG. 7 wherein the illumination surface comprises individual light-emitting pixels, one which serves as the first area of the illumination surface and the other of which serves as the second area of the illumination surface. Such a pixilated light-emitting illumination surface, if configured so that each light-emitting pixel could be sequenced on and off independently, can be used to create sequenced interpretation of the light measured at the image sensing pixel, distinguishing a straight light path from each of the many possible bent light paths. (It is noted that some light from the straight light path can diffuse, reflect, and/or refract within or from various constituents of the micro-organism or microscopic object and still end up incident on the same image sensing pixel as the straight path does). FIG. 9 depicts a larger scale view of the situation depicted in FIG. 8 wherein the illumination surface is an array of light-emitting elements and areas of both the illumination array and the image sensor array are depicted. The high-density array of light-emitting elements can comprise light-emitting diodes (LEDs), thin-film/printed organic light-emitting diodes (OLEDs), thin-film/printed organic light-emitting transistors (OLETs), etc. In various implementations the resolutions and spatial layout of the array of light-emitting elements can match, exceed, or be less than that of the image sensor pixel array as can be advantageous for reasons of function, cost, performance, etc. Further, the high-density array of light-emitting elements can comprise light-emitting elements of various wavelengths as can be advantageous in producing traditional optical color images and/or special scientific images. For example, should the microorganisms be provided with fluorescent markers prior to or within the flow microscope, ultraviolet wavelengths can be included (noting that ultraviolet LEDs are currently commercially available from manufacturers such as SET Inc., Photon Systems, etc.).

It is also noted that LEDs behave as (wavelength sensitive) photodiodes. Thus, an LED array can be used as an image sensing array. Additionally, individual elements in an LED array can be switched between idle mode, light-emitting mode, and light sensing mode. Such an arrangement, if used as an image sensor, can be sequentially operated to produce reflected-light contact imaging. In an implementation, the illuminating LED array is used both as a sequentially scanned light source and, via sequencing and/or multiplexing, as a reflective-imaging light sensor.

In the discussion, it is to be understood that organic light-emitting diodes (OLEDs) are a type of LED.

Additionally, although the discussion below cites LEDs in various light sensing roles, it is to be understood that light-sensing capabilities of various other types of known and future devices, including thin-film/printed organic light-emitting transistors (OLETs), Charge-Coupled Device (CCD) light sensors, Complementary Metal Oxide Semiconductor (CMOS) light sensors, can alternatively be employed where advantageous, where possible via adaptation and modifications, etc.

Although other devices can be used in the present invention, the surfaces depicted in FIG. 5 (and carrying through in subsequent discussion) can in particular be implemented as LED arrays. In some embodiments, the devices can be printed (for example, in the case of OLEDs). Further, although FIG. 5 and other figures presented depict or suggest a planar arrangement, it is to be understood that curved arrangements can also be used. It is noted that curved OLED arrays are currently in commercial production for use in displays in contemporary consumer electronics.

Figure 10:
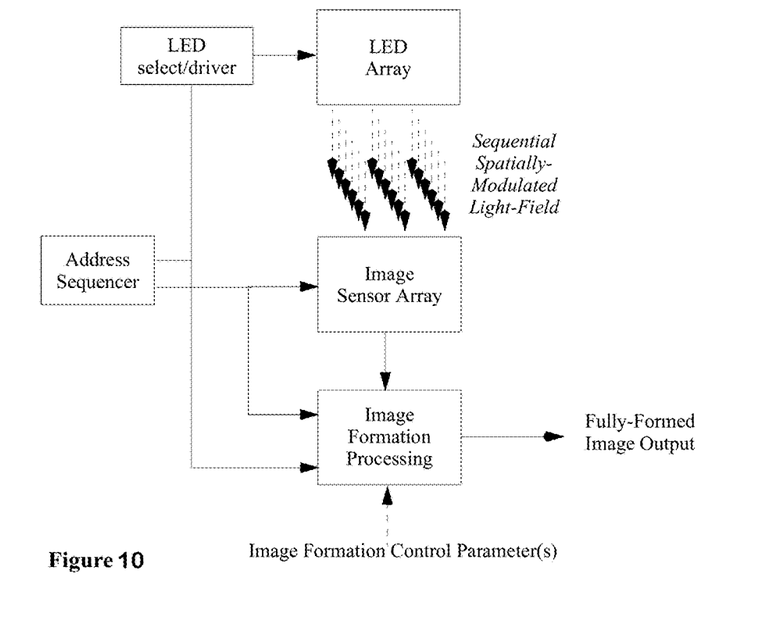
FIG. 10 depicts an exemplary embodiment of a synthetic image formation system employing the optical arrangement depicted in FIG. 9, the embodiment providing a fully-formed image output.
Figure 11:
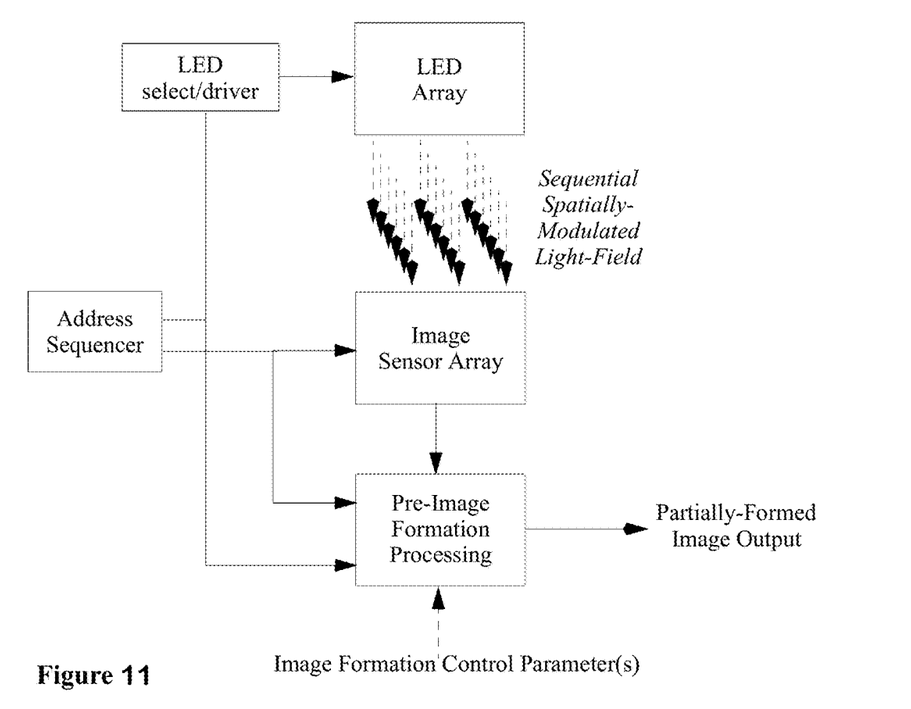
FIG. 11 depicts an exemplary embodiment of a synthetic image formation system employing the optical arrangement depicted in FIG. 9, the embodiment providing a partially-formed image output.
Figure 12:
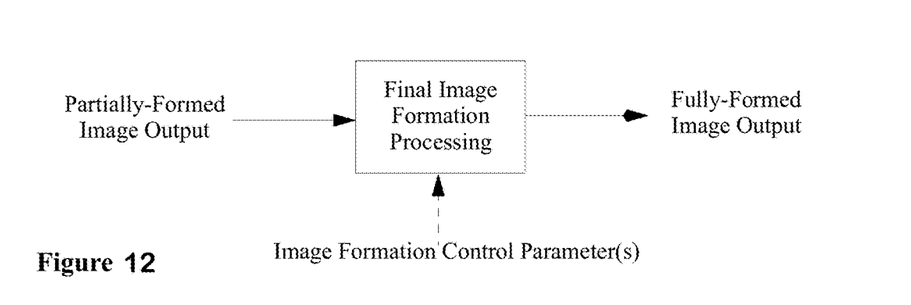
FIG. 12 depicts an exemplary arrangement wherein the partially-formed image output provided by an embodiment such as the exemplary depicted in FIG. 11 is further processed in a subsequent processing step by another processor so as to provide a fully-formed image output.

Referring to the arrangements described in at least terms of FIGS. 10-12, of particular interest is that by combining the temporal sequencing of individual light-emitting pixels with measurements at the optical sensor, the arrangements described above provide:

A means for obtaining a reasonably clear "traditional" optical transmission microscope type of image; and, even more interestingly The data measurement framework with which to implement various types of computed optical tomography.

In an embodiment, a common arrangement can be used for traditional optical transmission microscope imaging as well as at least some forms of computed tomography imaging.

FIG. 10 depicts a synthetic image formation system employing the optical arrangement depicted in FIG. 9.

The imaging sensor can be implemented (with or without lenses) in a 2-dimensional manner similar to the 1-dimensional imaging arrangements of a document scanner.

The source of illumination can be a light-emitting array, and the spatial light distribution can be fixed, time-varying, or modulated. For example, the illumination surface can be individual light-emitting pixels wherein the individual light-emitting pixels can be sequenced. Such sequencing permits spatial light field measurements that can be used in optical tomography. Accordingly, the invention provides data that can be used for optical tomography or used to produce tomography output.

The light-emitting array can provide sequenced spatially modulated illumination, the sequence operated as part of an imaging system producing fully-formed image output. In such embodiments, the array can produce a partially-formed image output that can be subsequent processed by another processor to produce fully-formed image output.

In some imaging implementations and applications, the material being imaged in the imaging region is thin in one dimension, for example as is commonly the case on conventional optical microscope slides. In such implementations and applications, the imaging sensing surface is configured to receive collimated light, or is proximate enough to the material being imaged in the imaging region that the light passing through the material being imaged in the imaging region is nearly collimated.

In such arrangements where the light passing through the material in the imaging region is nearly collimated or not collimated, algorithm-based lensless image formation algorithms, for example as taught in Pending U.S. patent application Ser. No. 12/419,229 (priority dates 1998-1999), Pending U.S. patent application Ser. No. 13/452,461 (priority date Apr. 20, 2011), and U.S. Pat. No. 8,305,480 (priority date May 22, 2008) can be used. As taught in Pending U.S. patent application Ser. No. 12/419,229, the algorithm-based lensless image formation arrangements and algorithms can include refraction effects, frequency domain techniques, deconvolution techniques, approximations, and employ a variety of micro-optic arrangements.

As indicated throughout, the above arrangements can be configured provide a platform for various types of optical microscopic tomography. Tomography arrangements are taught in U.S. patent application Ser. No. 12/817,107 and in pending U.S. patent application Ser. Nos. 13/963,917 and 13/963,931, both filed Aug. 9, 2013.

As taught in Pending U.S. patent application Ser. Nos. 12/419,229, 13/452,461, 12/817,107, 13/963,917 and 13/963,931 as well as in U.S. Pat. No. 8,305,480, the algorithmic image formation processes can be configured to provide control input. One example is the adjustment of the focus plane in imaging, while another is the selection of tomography image slicing, etc. Other examples include provisions for the adjustment of image parameters such as contrast, brightness, color correction, edge effect handling, etc. Further examples include the selection of light wavelength, controlling the superposition of two or more images, etc. Such control inputs are depicted in FIG. 10.

The various arrangements described and a wide range of variations and adaptions of them can be configured to provide fully-formed image output. Depending on the performance of various components, the system can produce individual or sequences of still images or live video-rate image streams.

FIG. 11 depicts a synthetic image formation system employing the optical arrangement of FIG. 9, and provides a partially-formed image output.

FIG. 12 depicts an arrangement wherein the partially-formed image output provided is further processed in a subsequent processing step of another processor to provide a fully-formed image output.

As mentioned earlier, arrays of OLED and other light-emission and light detection elements employed in various embodiments of the invention can be printed. This permits extremely low-cost manufacturing, and further readily accommodating an imaging region that (advantageously, necessarily, etc.) has at least one curved aspect to its shape.

Additionally, in that printed OLED displays can be fabricated that are optically transparent, the invention further provides for a variation in the aforedescribed arranges wherein aforedescribed image sensing surfaces are replaced with a series or stack of transparent OLED arrays, thus comprising a 3-dimensional light field sensor. For example, a stack of transparent OLED arrays can be fabricated to create a layered a 3-dimensional light field sensor. In one approach, each layer is fabricated on an associated transparent substrate, and the layers are assembled in a stacked arrangement. In another approach, layers of OLEDs are sequentially printed or otherwise deposited on a common substrate.

The resulting 3-dimensional light field sensor can be used to implement optical tomography using modifications to the algorithms accounting for the relative geometries between the illumination sources, the volume within an imaging region, and the location of various OLED locations within the 3-dimensional light field sensor.

In an example embodiment, a lensless microscopic imaging system for providing imaging, tomography, or both imaging and tomography of microscopic-scale objects is implemented, the microscopic imaging system comprising:

A imaging region comprising at least two transparent sides or areas;

A illumination surface in contact with one of the sides or areas of the imaging region; and A image sensing surface proximate with the other of the sides or areas of the imaging region, the image sensing surface receiving light fields from the image sensing surface and responsively creating electrical image signals;

wherein light from the illumination surface travels into the imaging region, producing a resulting light field affected by the contents of the imaging region, wherein the resulting light field is presented to the image sensing surface, and wherein the image sensing surface creates electrical image signals responsive to the resulting light field, and wherein the image sensing surface comprises no lenses and the light path between the imaging region and the image sensing surface does not pass through a lens element.

EXAMPLE APPLICATIONS

The present invention provides for small-sized, inexpensive, and innovative electronic imaging arrangements used for lensless and other micro-optic microscopy imaging and tomography, and can enable a very wide set of new possibilities and applications in the areas of microbiology, manufacturing, field medicine, material science, micro-fabrication, etc. The present invention can be implemented or adapted for use as a stand-alone laboratory instrument or for use as a component in other equipment, including microarrays, microplates, flow microscopes, cytometry systems, environmental and contamination monitoring systems, industrial monitoring instruments, food safety systems, etc.

As an example, as taught in Pending U.S. patent application Ser. No. 13/844,621 (priority date May 15, 2013), microscopic imaging arrangements can be built directly into the wells of micro arrays and microplates for performing imaging and tomography of cell cultures. Similar arrangements can be made for performing imaging and tomography of chemical processes, fermentation processes, bioreactor process, crystal promation processes, precipitation processes, etc.

As another example, the invention can also be incorporated into mobile devices such as those taught in Pending U.S. patent application Ser. No. 13/844,634 (priority date May 15, 2013), The arrangement can also be configured to be implanted or otherwise introduced into the body of an animal, plant, or human.

Closing

While the invention has been described in detail with reference to disclosed embodiments, various modifications within the scope of the invention will be apparent to those of ordinary skill in this technological field. It is to be appreciated that features described with respect to one embodiment typically can be applied to other embodiments.

The invention can be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. Therefore, the invention properly is to be construed with reference to the claims.

I claim:

1. A lensless microscopic imaging system for providing imaging or tomography of microscopic-scale non-moving objects, the microscopic imaging system comprising:
   an imaging region comprising at least two transparent areas;
   an illumination surface in contact with one of the areas of the imaging region; and
   a 2-dimensional imaging sensor comprised by an array of light-emitting diodes (LEDs) proximate with another side of the imaging region, the 2-dimensional imaging sensor receiving light fields from the imaging region and responsively creating electrical image signals;
   wherein the illumination surface comprises an array of light-emitting elements, wherein the light-emitting elements are illuminated sequentially providing spatially modulated illumination, and wherein light from the illumination surface travels into the imaging region, producing a resulting light field affected by contents of the imaging region,
   wherein the resulting light field is presented to the 2-dimensional imaging sensor, and
   wherein the 2-dimensional imaging sensor creates electrical image signals responsive to the resulting light field, and wherein the 2-dimensional imaging sensor comprises no lenses and a light path between the imaging region and the 2-dimensional imaging sensor does not pass through a lens element.

2. The microscopic imaging system of claim 1 wherein the illumination surface is electrically powered.

3. The microscopic imaging system of claim 1 wherein the illumination surface comprises an array of light-emitting diodes (LEDs).

4. The microscopic imaging system of claim 1 wherein the illumination surface comprises an array of Organic Light Emitting Diodes (LEDs).

5. The microscopic imaging system of claim 1 wherein the illumination surface comprises an array of Organic Light Emitting Transistors (OLETs).

6. The microscopic imaging system of claim 1 wherein a light-emitting element in the array of light-emitting elements also serves as a light sensor.

7. The microscopic imaging system of claim 6 wherein the array of light-emitting elements also serves as an image sensor.

8. The microscopic imaging system of claim 1 wherein the sequential illumination of the light-emitting elements in the array of light-emitting elements is used in image formation.

9. The microscopic imaging system of claim 8 wherein the image formation produces a fully-formed image output.

10. The microscopic imaging system of claim 8 wherein the image formation produces a partially-formed image output.

11. The microscopic imaging system of claim 10 wherein the partially-formed image output is subsequently processed by a processor to produce a fully-formed image output.

12. The microscopic imaging system of claim 8 wherein the image formation is responsive to a received control signal.

13. The microscopic imaging system of claim 1 wherein the system is configured to produce optical tomography.

14. The microscopic imaging system of claim 1 wherein the system is configured to produce an output that can be used in optical tomography.

15. The microscopic imaging system of claim 1 wherein at least one of the transparent areas comprises a curved surface.

16. The microscopic imaging system of claim 1 wherein the 2-dimensional imaging sensor comprises an array of Organic Light Emitting Diodes (OLEDs).

17. The microscopic imaging system of claim 1 wherein the array of light-emitting elements comprised by the illumination surface is arranged so that it can be used both as a sequentially scanned light source and as a reflective-imaging light sensor.

18. The microscopic imaging system of claim 1 wherein the system is arranged so that operation of the illumination surface employs sequencing of light sensing and light emitting modes of the light-emitting elements.

19. The microscopic imaging system of claim 1 wherein the system is arranged so that operation of the 2-dimensional imaging sensor employs multiplexing of light sensing and light emitting modes of the LEDs.

20. The microscopic imaging system of claim 1 wherein the system is configured so a common arrangement can be used for traditional optical transmission microscope imaging as well as at least some forms of computed tomography imaging.

* * * * *